US008761490B2

(12) United States Patent
Scheid et al.

(10) Patent No.: US 8,761,490 B2
(45) Date of Patent: Jun. 24, 2014

(54) SYSTEM AND METHOD FOR AUTOMATED BORESCOPE INSPECTION USER INTERFACE

(75) Inventors: Paul Raymond Scheid, West Hartford, CT (US); Richard C. Grant, Ellington, CT (US); Alan Matthew Finn, Hebron, CT (US); Hongcheng Wang, Vernon, CT (US); Ziyou Xiong, Wethersfield, CT (US)

(73) Assignee: United Technologies Corporation, Hartford, CT (US)

( * ) Notice: Subject to any disclaimer, the term of this patent is extended or adjusted under 35 U.S.C. 154(b) by 200 days.

(21) Appl. No.: 13/288,606

(22) Filed: Nov. 3, 2011

(65) Prior Publication Data
US 2013/0113914 A1 May 9, 2013

(51) Int. Cl.
*G06K 9/00* (2006.01)

(52) U.S. Cl.
USPC .......................................................... 382/145

(58) Field of Classification Search
None
See application file for complete search history.

(56) References Cited

U.S. PATENT DOCUMENTS

| | | |
|---|---|---|
| 5,070,401 A | 12/1991 | Salvati et al. |
| 5,619,429 A | 4/1997 | Aloni et al. |
| 5,774,212 A | 6/1998 | Corby |
| 6,153,889 A | 11/2000 | Jones |
| 6,362,875 B1 | 3/2002 | Burkley |
| 6,424,733 B2 | 7/2002 | Langley |
| 7,099,078 B2 | 8/2006 | Spencer |
| 7,489,811 B2 | 2/2009 | Brummel et al. |
| 7,518,632 B2 | 4/2009 | Konomura |
| 7,564,626 B2 | 7/2009 | Bendall et al. |
| 7,619,728 B2 | 11/2009 | Ogburn et al. |
| 7,656,445 B2 | 2/2010 | Heyworth |
| 7,758,495 B2 | 7/2010 | Pease et al. |
| 2002/0128790 A1 | 9/2002 | Woodmansee |
| 2003/0063270 A1 | 4/2003 | Hunik |
| 2004/0183900 A1* | 9/2004 | Karpen et al. ................. 348/92 |
| 2004/0242961 A1 | 12/2004 | Bughici |
| 2005/0016857 A1 | 1/2005 | Kovarsky et al. |
| 2005/0129108 A1 | 6/2005 | Bendall et al. |
| 2006/0050983 A1 | 3/2006 | Bendall et al. |
| 2006/0115143 A1 | 6/2006 | Auerbach |
| 2011/0013846 A1 | 1/2011 | Hori |
| 2011/0025844 A1* | 2/2011 | Hori ............................ 348/135 |
| 2011/0026805 A1 | 2/2011 | Hori |
| 2011/0211940 A1 | 9/2011 | George et al. |

FOREIGN PATENT DOCUMENTS

WO      WO 2010/020338 A1      2/2010

OTHER PUBLICATIONS

Candès, Emmanuel J., et al. "Robust principal component analysis?." arXiv preprint arXiv:0912.3599 (2009).*
International Search Report from corresponding Application No. PCT/US2012/062655. Report dated Jan. 21, 2013.

* cited by examiner

*Primary Examiner* — Stephen R Koziol
*Assistant Examiner* — Amandeep Saini
(74) *Attorney, Agent, or Firm* — Miller, Matthias & Hull LLP

(57) ABSTRACT

A system and method for improving human-machine interface while performing automated defect detection is disclosed. The system and method may include an image capture device for capturing and transmitting data of an object, performing automated analysis of the data and reviewing results of the automated analysis by a human inspector and providing feedback. The system and method may further include refining the automated analysis of the data based upon the feedback of the human inspector.

18 Claims, 2 Drawing Sheets

SYSTEM AND METHOD FOR AUTOMATED BORESCOPE INSPECTION USER INTERFACE

TECHNICAL FIELD OF THE DISCLOSURE

The present disclosure relates to automated inspection techniques and, more particularly, relates to automated visual inspection techniques of images or videos captured by image capture devices such as borescopes.

BACKGROUND OF THE DISCLOSURE

Video inspection systems, such as borescopes, have been widely used for capturing images or videos of difficult-to-reach locations by "snaking" image sensor(s) to these locations. Applications utilizing borescope inspections include aircraft engine blade inspection, power turbine blade inspection, internal inspection of mechanical devices and the like.

A variety of techniques for inspecting the images or videos provided by borescopes for determining defects therein have been proposed in the past. Most such techniques capture and display images or videos to human inspectors for defect detection and interpretation. Human inspectors then decide whether any defect within those images or videos exists. These techniques are prone to errors resulting from human inattention. Some other techniques utilize automated inspection techniques in which most common defects are categorized into classes such as leading edge defects, erosion, nicks, cracks, or cuts and any incoming images or videos from the borescopes are examined to find those specific classes of defects. These techniques are thus focused on low-level feature extraction and to identify damage by matching features. Although somewhat effective in circumventing errors from human involvement, categorizing all kinds of blade damage defects within classes is difficult and images having defects other than those pre-defined classes are not detected.

Accordingly, it would be beneficial if an improved technique for performing defect detection was developed. It would additionally be beneficial if such a technique provided an improved user interface to minimize human intervention and/or assist human inspectors in defect interpretation.

SUMMARY OF THE DISCLOSURE

In accordance with one aspect of the present disclosure, a method of improving automated defect detection is disclosed. The method may include providing an image capture device for capturing and transmitting data of an object, performing automated analysis of the data, reviewing results of the automated analysis by a human inspector and providing feedback and refining the automated analysis of the data based upon the feedback of the human inspector.

In accordance with another aspect of the present disclosure, a system for performing automated defect detection is disclosed. The system may include an image capture device for capturing and transmitting images of one or more components of an object and a monitoring and analysis site in at least indirect communication with the image capture device, the monitoring and analysis site capable of performing an automated analysis of the images. The system may also include a database for selectively storing results of the automated analysis.

In accordance with yet another aspect of the present disclosure, a method of performing automated defect detection is disclosed. The method may include providing an image capture device capable of capturing and transmitting a sequence of images of one or more blades of an engine and performing an automated analysis on the sequence of images. The automated analysis may include performing a Robust Principal Component Analysis on the sequence of images to generate analysis results and utilizing a classifier to classify the analysis results into defects or non-defects by generating an output. The method may further include verifying the defects or non-defects by a human inspector and providing feedback and training the classifier based upon the feedback from the human inspector.

While the present disclosure is susceptible to various modifications and alternative constructions, certain illustrative embodiments thereof will be shown and described below in detail. It should be understood, however, that there is no intention to be limited to the specific embodiments disclosed, but on the contrary, the intention is to cover all modifications, alternative constructions, and equivalents falling within the spirit and scope of the present disclosure.

DETAILED DESCRIPTION OF THE DISCLOSURE

Figure 1:
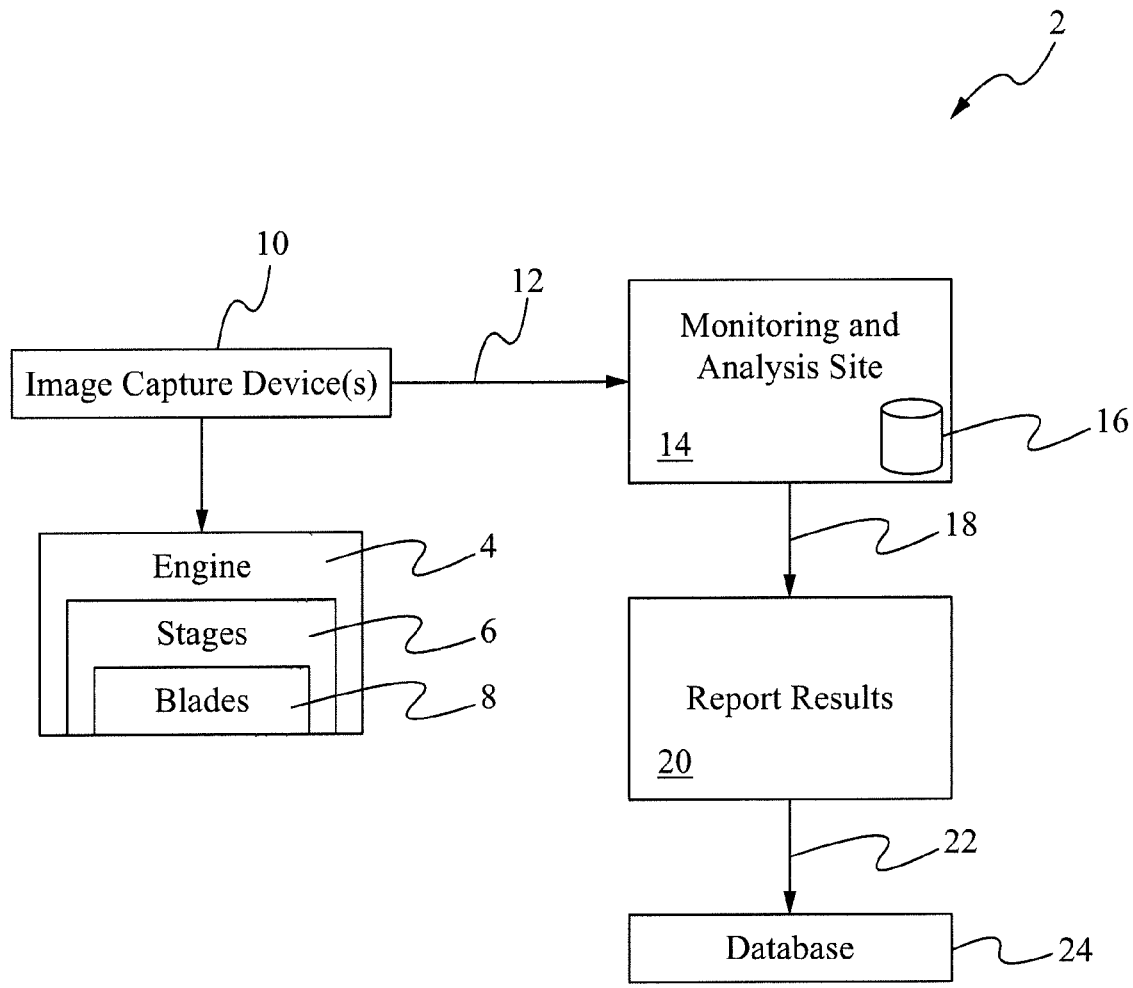
FIG. 1 is a schematic illustration of an automated defect detection system, in accordance with at least some embodiments of the present disclosure.

Referring to FIG. 1, a schematic illustration of an automated defect detection system 2 is shown, in accordance with at least some embodiments of the present disclosure. In at least some embodiments, the automated defect detection system 2 may be an automated borescope inspection (ABI) system. As shown, the automated defect detection system 2 may include an engine 4 having a plurality of stages 6, each of the stages having a plurality of blades 8, some or all of which may require visual inspection periodically at predetermined intervals, or based on other criteria by an image capture device 10. The engine may be representative of a wide variety of engines such as jet aircraft engines, aeroderivative industrial gas turbines, steam turbines, diesel engines, automotive and truck engines, and the like. Notwithstanding the fact that the present disclosure has been described in relation to visual inspection of the blades 8 of the engine 4, in other embodiments, the ABI system 2 may be employed to inspect other parts of the engine inaccessible by other means, as well as to perform inspection in other equipment and fields such as medical endoscope inspection, inspecting critical interior surfaces in machined or cast parts, forensic inspection, inspection of civil structures such as buildings bridges, piping, etc.

The image capture device 10 may be an optical device having an optical lens or other imaging device or image sensor at one end and capable of capturing and transmitting still images or video images (referred hereinafter to as "data") through a communication channel 12 to a monitoring and analysis site 14. The image capture device 10 may be representative of any of a variety of flexible borescopes or fiberscopes, rigid borescopes, video borescopes or other devices, such as endoscopes, which are capable of capturing and transmitting images or videos of difficult-to-reach areas through the communication channel 12. The communication channel 12 in turn may be an optical channel or alternatively, may be any other wired, wireless or radio channel or any other type of channel capable of transmitting data between two points including links involving the World Wide Web (www) or the internet.

With respect to the monitoring and analysis site 14, it may be located on-site near or on the engine 4, or alternatively, it may be located on a remote site away from the engine. Furthermore, the monitoring and analysis site 14 may include one or more processing systems 16 (e.g., computer systems having a central processing unit and memory) for recording, processing and storing the data received from the image capture device 10, as well as personnel for controlling operation of the one or more processing systems. Thus, the monitoring and analysis site 14 may receive the data of the blades 8 captured and transmitted by the image capture device 10 via the communication channel 12. Upon receiving the data, the monitoring and analysis site 14 and, particularly, the one or more processing systems 16 may process that data to determine any defects within any of the blades 8. Results (e.g., the defects) 20 may then be reported through communication channel 18. In addition to reporting any defects in any of the blades 8, the results 20 may also relay information about the type of defect, the location of the defect, size of the defect, metrology about the blade 8, etc.

Similar to the communication channel 12, the communication channel 18 may be any of variety of communication links including wired channels, optical or wireless channels, radio channels or possibly links involving the World Wide Web (www) or the internet. It will also be understood that although the results 20 have been shown as being a separate entity from the monitoring and analysis site 14, this need not always be the case. Rather, in at least some embodiments, the results 20 may be stored within and reported through the monitoring and analysis site 14 as well. Furthermore, in at least some embodiments, the results 20 may be stored via communication channel 22 (which may be similar to the communication channels 12 and 18) within a database 24 for future reference, as well as for raising alarms when defects are detected. As will be described further below, the database 24 may also be updated/trained to refine the processing techniques of the one or more processing systems 16 in identifying defects. The database 24 may also be employed for selectively retrieving information therefrom.

Figure 2:
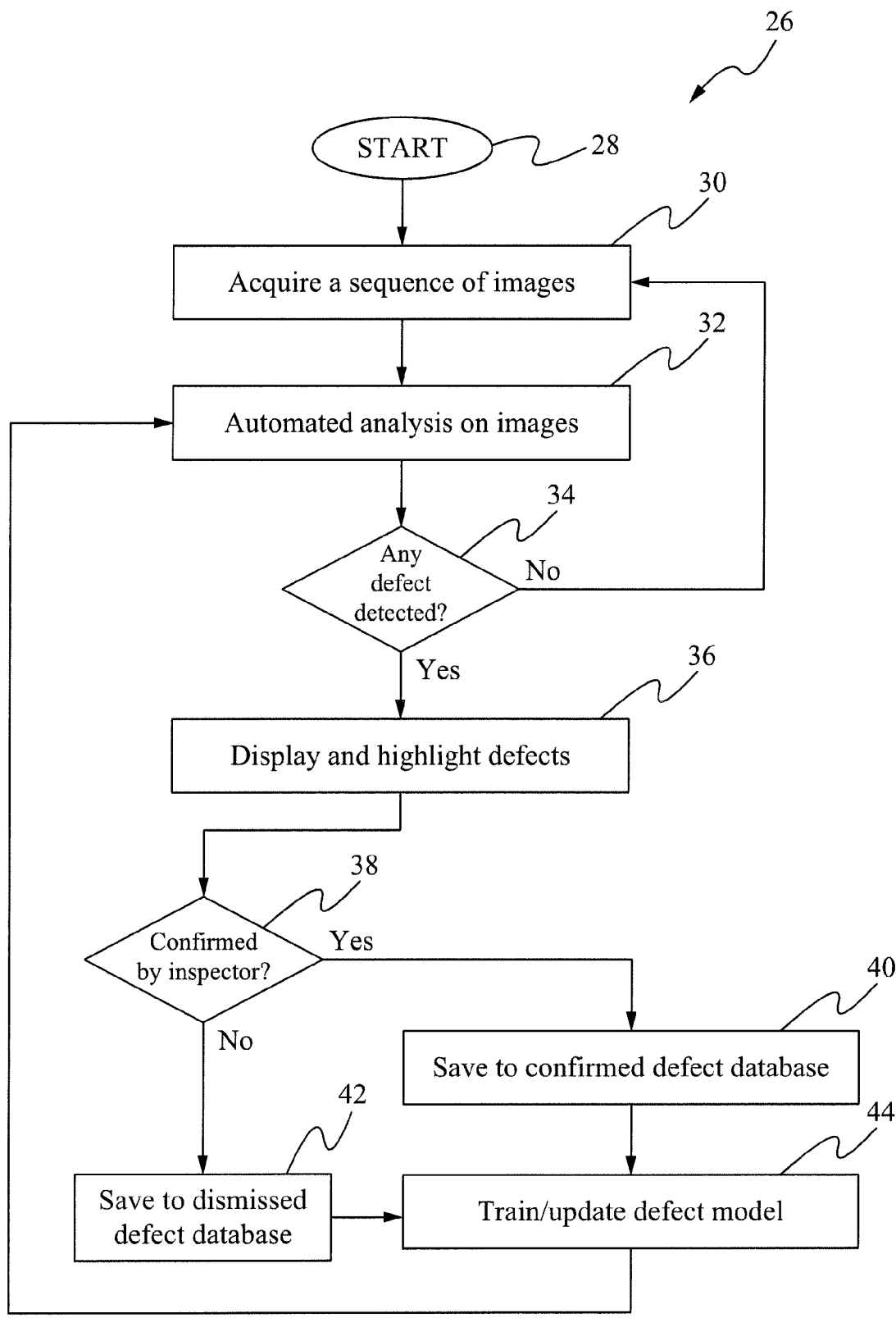
FIG. 2 is a flowchart outlining steps of improving human-machine interface while performing the automated defect detection using the automated defect detection system of FIG. 1, in accordance with at least some embodiments of the present disclosure.

Referring now to FIG. 2, a flowchart 26 outlining sample steps which may be followed in improving the human-machine interface while performing the automated defect detection using the automated defect detection system 2 is shown, in accordance with at least some embodiments of the present invention. As shown, after starting at a step 28, the process may proceed to a step 30, where a sequence of images of one or more of the blades 8 may be obtained. As described above, the sequence of images may be still images or video images of the blades 8. Furthermore, the images may be sequential images in terms of the order in which they are captured by the image capture device 10 (i.e., image one, followed by image two, etc.) or, alternatively, the images may be non-sequential with regard to the order in which the images were captured by the image capture device. For example, instead of capturing and transmitting every image in a sequential order, every third image captured by the image capture device 10 may be captured and transmitted.

Moreover, the sequence of images may be obtained by either rotating the image capture device 10 relative to the engine 4 to capture images of each blade row (e.g., each one of the stages 6 may be termed as one blade row) or, alternatively, the engine may be rotated in a full or a partial turn towards or away from the image capture device to capture the images. It will be understood that a sequence of images of all or a subset of blades or even a single blade may be obtained for each of the stages 6 for performing an automated analysis on those images, as outlined in step 32 below. The images of the blades from more than one of the stages 6 may also be obtained. The images captured by the image capture device 10 at the step 30 may then be transmitted to the monitoring and analysis site 14 via the communication channel 12.

Upon receiving the sequence of images from the step 30, an automated analysis of those images may be performed at the step 32 by the one or more processing systems 16 of the monitoring and analysis site 14. In at least some embodiments, a Robust Principal Component Analysis (PCA) technique for performing the automated analysis of the images may be employed. Specifically, using the Robust PCA technique, each of the sequences of images may be decomposed into a low rank matrix (or a low rank part) and a sparse matrix (or a sparse part). The low rank matrix may contain a normal part or region of that particular blade image, while the sparse matrix may contain an anomaly or defect of that blade image. After separating each of the sequences of images into the low rank matrix and the sparse matrix, the sparse matrix may be further processed to confirm whether the data in the sparse matrix corresponds to any physical damages or defects. Notwithstanding the fact that in the present embodiment, a Robust PCA technique for performing the automated analysis of the sequence of images obtained at the step 30 is employed, in other embodiments, other techniques suitable for performing such analyses may be employed as well.

In addition to performing the Robust PCA, the automated analysis may also implement a classifier that may be utilized for confirming and verifying the results (e.g., potential defects or potential non-defects) of the automated analysis and may be trained (e.g., refined) to improve accuracy thereof in classifying the potential defects and potential non-defects into defects and non-defects. In at least some embodiments, the classifier may be implemented as a mathematical expression that may utilize the results of the automated analysis and may classify the results of the automated analysis into defects or non-defects and may report that classification as a certainty, an uncertainty, or as a binary output. Thus, for example, if the automated analysis technique finds a potential defect within the blades 8 corresponding to the sequence of images received at the step 30, then the classifier may classify those results as a defect and may output a binary value of one (1). On the other hand, if the automated analysis did not find any potential defect, the classifier may classify those results as a non-defect and may output a binary value of zero (0). Further, the classifier may report a non-binary value representative, for instance, of a certainty or uncertainty on a scale of zero (0) to one (1). In addition and, as will be described further below, even though the automated analysis may obtain a result of a potential defect (or a potential non-defect), the classifier may still classify those results as a non-defect (or defect), respectively, based upon feedback and training received from human inspectors.

The classifier may be implemented in any of a variety of ways provided that the technique chosen is compatible with the automated analysis technique of the step 32. In at least some embodiments, the classifier may be a support vector machine classifier, while in other embodiments the classifier may be a neural net classifier, a bayesian classifier, and the like. Classifiers other than those mentioned above may be employed in alternate embodiments.

Next, at a step 34, it is determined whether the automated analysis of the sequence of images performed at the step 32 and the classification of the classifier resulted in any defects being found. Defects may include the type of defect such as leading edge defects, erosions, nicks, dents, cracks or cuts, the location of the defects, the size of the defects, and other defect parameters. Depending upon the output of the classifier at the step 32, a defect or a non-defect at the step 34 may be determined. For example, if the classifier outputs a binary value of zero (0), then the one or more processing systems 16 may determine that no defect was found during the automated analysis of the step 32 and in that case, the process loops back to the step 30 in order to receive the next batch of images and continue the process described above. On the other hand, if the classifier outputs a binary value of one (1), then the one or more processing systems 16 may determine that a defect is indeed discovered during the automated analysis performed at the step 32, and the process may proceed to a step 36. Relatedly, if the classifier computes a certainty or uncertainty between zero (0) and one (1), then that certainty may be resolved as indicating either a defect or non-defect, for instance, by comparing to a threshold. At the step 36, the defects, and any certainty or uncertainty if known, may be displayed and highlighted to one or more human inspectors for their review.

Then, at a step 38, the displayed defects may be verified by the human inspectors who may reject, confirm, or indicate further manual or automatic analysis of the results to be performed. If the results of the step 34 are confirmed by the inspectors at the step 38, then at a step 40, the results may be saved to a confirmed defect database. The confirmed defect database may be part of the database 24 and may be utilized by the classifier at the step 32 to classify the potential defects or potential non-defects generated by the Robust PCA into defects or non-defects. Thus, at the steps 32 and 34, the classifier may receive the results of the automatic analysis of the step 32 and may compare and correlate those results with the values stored within the confirmed defect database. If the automated analysis results in a potential defect being determined and if a hit between the results of the automatic analysis and the values of the confirmed defect database is found, the classifier may output a defect by way of a binary value of one (1). On the other hand, if the automated analysis determined a potential defect and if no hit with the confirmed defect database is found, the classifier may classify the potential defect as a non-defect and output a binary value of zero (0). Similarly, if the automated analysis generated a potential non-defect but if the classifier found a hit with the confirmed defect database, then the classifier may generate a binary value of one (1) to indicate a defect.

Relatedly, if at the step 38, the results of the step 34 are rejected by the human inspectors, then those results may be stored within a dismissed defect database at a step 42, which similar to the confirmed defect database, may be part of the database 24 and may be utilized by the classifier at the steps 32 and 34 in classifying the potential defects or potential non-defects into defects or non-defects. Thus, if the automated analysis at the step 32 determines a potential defect, as described above, the classifier may compare those results with the values within the confirmed defect database. If no hit is found within the confirmed defect database, the classifier may look and compare the results of the automated analysis with the values stored within the dismissed defect database. If a hit occurs between the results of the automated analysis and the dismissed defect database, the classifier may output a binary value of zero (0) indicating a no defect even though the automated analysis determined a potential defect within the sequence of images of the step 30.

Similarly, if no potential defect is determined by the automated analysis at the steps 32 and 34, the classifier may still classify the potential non-defect as a defect if a hit for the results of the automated analysis is found within the confirmed defect database, as described above. Likewise, if the automated analysis determines a potential defect, but the classifier finds a hit within the dismissed defect database, then the classifier may classify the potential defect as a non-defect.

Next, at a step 44, based upon the review and verification of the results of the automated analysis by the human inspectors, and the classification of the review into the confirmed defect database and the dismissed defect database at the steps 40 and 42, respectively, the classifier at the steps 32 and 34 may be trained or refined to improve the accuracy of the automated analysis technique performed in reporting potential defects or non-defects and classifying those as defects and non-defects. As the confirmed defect and the dismissed defect databases continue to be updated, the accuracy of the classifier in classifying defects or non-defects improves as well, thereby improving the human-machine or user interface in performing the automated defect detection. From the step 44, the process may loop back to the step 32 to continue analyzing sequence of images from the step 30 to determine defects or non defects within the blades 8.

The training, re-training, or refining of the classifier used in the step 34 may be accomplished by repeating the initial training procedure, on-line or off-line, using the original database plus the confirmed defect database and the dismissed defect database or by just using the confirmed defect database and the dismissed defect database. The training procedure may be performed by utilizing one or more of commonly known procedures such as Support Vector Machine (SVM) training, Radial Basis Function (RBF) classifier training, Constructive Learning Algorithm (CLA) RBF training, neural network training, etc.

Industrial Applicability

In general, the present disclosure sets forth a system and method for improving human-machine interface while performing an automated defect detection. The system and method may include providing a image capture device for capturing and transmitting images of blades of an engine to a monitoring and analysis site. Using the information exported by the image capture device, an automated analysis of the images may be performed and defects within the blades may be determined. Instead of having human inspectors look at many similar images of very similar blades of an engine stage, the above method first uses advanced image analysis algorithms (such as Robust PCA) to analyze these images, identify images of potential defects, and prompts human inspectors to review these images for verification. The aforementioned method also allows the human inspectors or users to accept, reject, or indicate further manual or automated analysis of the results obtained by the image analysis algorithms. The review results of the human inspectors may then be recorded into databases, which may be updated with confirmed defects or dismissed defects to further train the image analysis algorithms.

The disclosed approach relieves human inspectors of examining many similar images of very similar components of a physical device, reducing misses due to human error. It applies image analysis techniques to filter out a majority of the images without defects before prompting human inspectors to pay attention to images of potential defects.

The disclosed approach furthermore makes use of human inspectors' feedback on what are real defects and what are defects that can be safely dismissed to improve the accuracy of the automated statistical image analysis module. Moreover, although the above technique teaches training the classifier in real-time, in at least some embodiments, the classifier may be trained offline by utilizing data from prior automated analysis results.

While only certain embodiments have been set forth, alternatives and modifications will be apparent from the above description to those skilled in the art. These and other alternatives are considered equivalents and within the spirit and scope of this disclosure and the appended claims.

What is claimed is:

1. A method of improving automated defect detection, the method comprising:
   providing an image capture device for capturing and transmitting video images of an object in motion in a device;
   performing automated Robust Principal Component Analysis on the video images to simultaneously decompose the video images into a low rank matrix representing a normal object and a sparse matrix representing an object anomaly;
   processing the sparse matrix to determine potential defects or potential non-defects;
   reviewing results of the automated analysis by a human inspector and providing feedback; and
   refining the automated analysis on the data based upon the feedback of the human inspector.

2. The method of claim 1, wherein performing the automated analysis of the data comprises:
   classifying the potential defects or potential non-defects into defects or non-defects.

3. The method of claim 2, wherein classifying the potential defects or the potential non-defects comprises:
   providing a classifier that utilizes the potential defects or the potential non-defects from the Robust Principal Component Analysis as an input; and
   generating at least one of a certainty, an uncertainty and a binary output to classify the potential defects or the potential non-defects into the defects or the non-defects.

4. The method of claim 3, wherein the classifier outputs a binary value of one if the classifier classifies the potential defects or the potential non-defects into the defects.

5. The method of claim 3, wherein the classifier outputs a binary value of zero if the classifier classifies the potential defects or the potential non-defects into the non-defects.

6. The method of claim 1, wherein the object is a plurality of jet engine blades within one stage of the jet engine.

7. The method of claim 1, wherein reviewing the results of the automated analysis by a human inspector comprises one of accepting and rejecting the results of the automated analysis.

8. The method of claim 7, wherein accepting the results of the automated analysis comprises saving the results within a confirmed defect database.

9. The method of claim 7, wherein rejecting the results of the automated analysis comprises saving the results within a dismissed defect database.

10. The method of claim 1, wherein reviewing the results of the automated analysis by a human inspector comprises indicating further manual or automated analysis to be performed on the data.

11. The method of claim 1, wherein refining the automated analysis comprises updating one of a confirmed defect database and a dismissed defect database and revising the automated analysis based on the updated database to improve accuracy of the automated analysis.

12. A system for performing automated defect detection, the system comprising:
   an image capture device configured to capture and transmit video images of one or more moving components of an object; and
   a monitoring and analysis site in at least indirect communication with the image capture device, the monitoring and analysis site configured to perform an automated analysis of the video images using Robust Principal Component Analysis on the video images to simultaneously decompose the video images into a low rank matrix representing a normal component and a sparse matrix representing a component anomaly and to process the sparse matrix to determine potential defects or potential non-defects; and
   a database configured to store results of the automated analysis.

13. The system of claim 12, wherein the object is at least one of an engine and a turbine comprising a plurality of stages, each of the plurality of stages having a plurality of blades.

14. The system of claim 12, wherein the monitoring and analysis site is a remote site.

15. A method of performing automated defect detection, the method comprising:
   providing an image capture device configured to capture and transmit a sequence of video images of one or more rotating blades of an engine;
   performing an automated analysis on the sequence of video images, the automated analysis comprising (a) performing a Robust Principal Component Analysis on the sequence of video images to simultaneously decompose the video images into a low rank matrix representing a normal blade and a sparse matrix representing a blade anomaly and to generate analysis results by processing the sparse matrix to determine potential defects or potential non-defects; and (b) utilizing a classifier to classify the analysis results into defects or non-defects by generating an output;
   verifying the defects or the non-defects by a human inspector and providing feedback; and
   re-training the classifier based upon the feedback from the human inspector.

16. The method of claim 15, wherein the defects comprises one or more of a type of the defect, a location of the defect, and a size of the defect.

17. The method of claim 16, wherein the type of the defect may be one or more of leading edge defects, erosions, nicks, cracks, dents, and cuts.

18. The method of claim 15, wherein providing feedback comprises one of (a) accepting the output of the classifier and storing the output into a confirmed defect database; (b) rejecting the output of the classifier and storing the output into a dismissed defect database; and (c) indicating further manual or automated analysis to be performed.

* * * * *